US00PP21009P2

(12) United States Plant Patent
van Rijn

(10) Patent No.: US PP21,009 P2
(45) Date of Patent: May 25, 2010

(54) *BOUGAINVILLEA* PLANT NAMED 'RIJNBO710'

(50) Latin Name: *Bougainvillea spectabilis*
Varietal Denomination: RIJNBO710

(76) Inventor: Leonardus van Rijn, Leo@Rijnplant.com Hofzichtlaan 5, De Lier NL-2676 (NL)

( * ) Notice: Subject to any disclaimer, the term of this patent is extended or adjusted under 35 U.S.C. 154(b) by 0 days.

(21) Appl. No.: 12/221,438

(22) Filed: Aug. 2, 2008

(51) Int. Cl.
*A01H 5/00* (2006.01)

(52) U.S. Cl. ..... Plt./256

(58) Field of Classification Search ..... Plt./256
See application file for complete search history.

*Primary Examiner*—Kent L Bell

(57) ABSTRACT

A new and distinct *Bougainvillea spectabilis* cultivar named 'RIJNBO710' is disclosed, characterized by strong, long-lasting purple flowers and a compact plant shape. The new variety is a *Bougainvillea spectabilis*, and naturally blooms continuously from Spring through Fall.

1 Drawing Sheet

Figure 1:
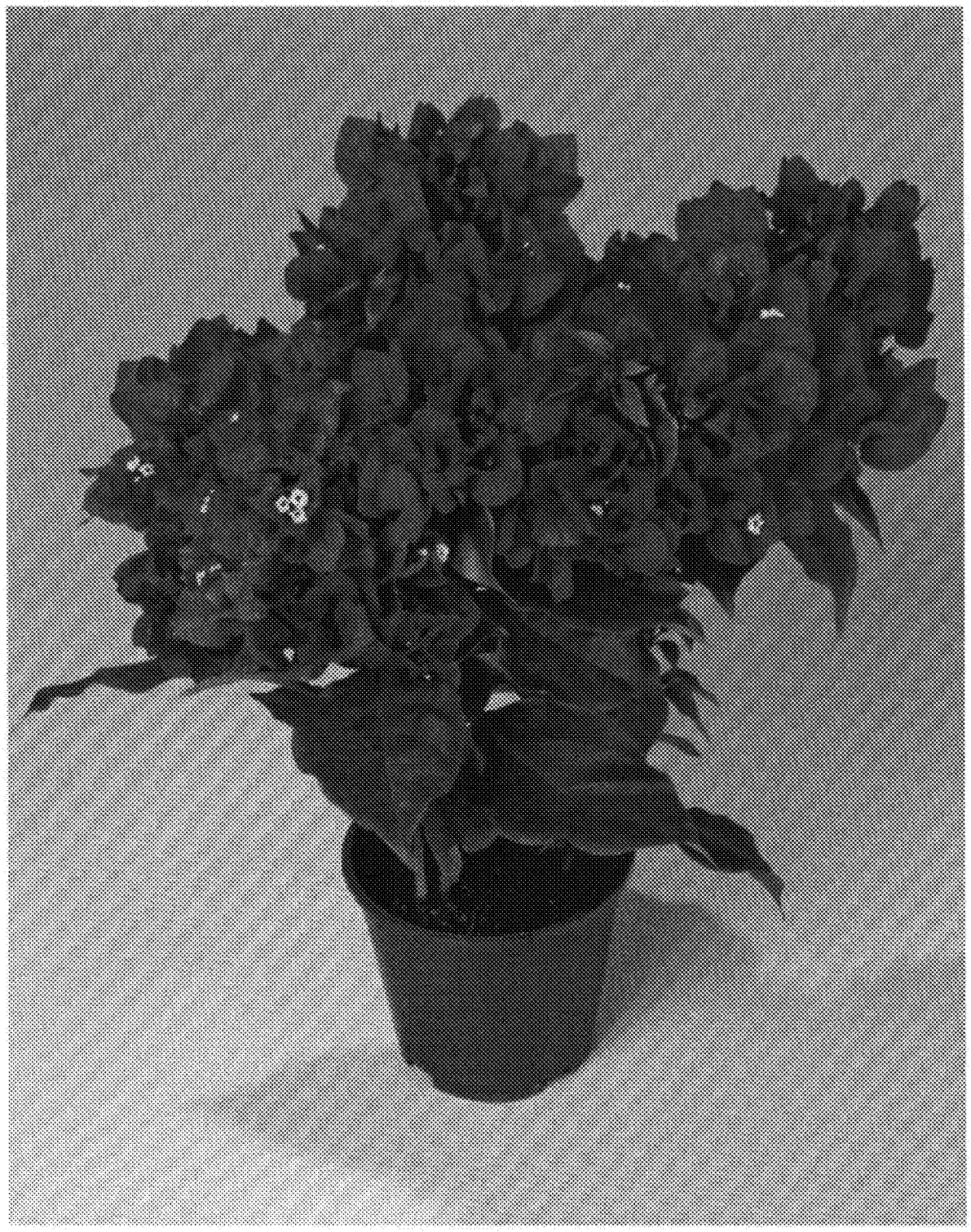

Latin name of the genus and species: *Bougainvillea spectabilis.*

Variety denomination: 'RIJNBO710'.

BACKGROUND OF THE INVENTION

The new cultivar is the product of a planned breeding program under the direction of the inventor, Leonardus van Rijn, a citizen of Holland. The objective of the breeding program was to produce plants of *Bougainvillea spectabilis* with compact plant habits. The new variety is a naturally occurring whole plant mutation of the variety *Bougainvillea spectabilis* 'Vera Deep Purple,' U.S. Plant Pat. No. 15,429. The new variety was discovered May 2006 by the inventor in a commercial greenhouse, in De Lier, the Netherlands.

Asexual reproduction of the new cultivar 'RIJNBO710' by vegetative cuttings was performed in De Lier, the Netherlands, in November 2006 and has shown that the unique features of this cultivar are stable and reproduced true to type through several successive generations.

SUMMARY OF THE INVENTION

The cultivar 'RIJNBO710' has not been observed under all possible environmental conditions. The phenotype may vary somewhat with variations in environment such as temperature, day length, and light intensity, without, however, any variance in genotype.

The following traits have been repeatedly observed and are determined to be the unique characteristics of 'RIJNBO710' These characteristics in combination distinguish 'RIJNBO710' as a new and distinct *Bougainvillea spectabilis* cultivar:

1. Compact plant.
2. Strong plant with branches resistant to breakage.
3. Distinctive purple flower coloration.

PARENT COMPARISON

Plants of the new cultivar 'RIJNBO710' are similar to plants of the parent variety, 'Vera Deep Purple,' U.S. Plant Pat. No. 15,429 in most horticultural characteristics, however, plants of the new cultivar 'RIJNBO710' produce flowers that are thicker, stronger and more durable than the parent variety. Flowers of the new variety also last longer on the plant than flowers of the parent variety. Additionally, the new variety produces leaves that are thicker and more durable than the parent variety.

The parent variety is also the best commercial comparison.

BRIEF DESCRIPTION OF THE PHOTOGRAPH

The accompanying photograph in FIG. 1 illustrates in full color a typical plant of 'RIJNBO710' grown in a greenhouse. The pot size is a commercial 17 cm container, approximately. The plant shown is approximately 1 year old. The photograph was taken using conventional techniques and although colors may appear different from actual colors due to light reflectance it is as accurate as possible by conventional photographic techniques.

DETAILED BOTANICAL DESCRIPTION

In the following description, color references are made to The Royal Horticultural Society Colour Chart except where general terms of ordinary dictionary significance are used. The following observations and measurements describe 'RIJNBO710' plants grown in a commercial greenhouse in De Lier, The Netherlands from March 2007 to June 2007. The growing temperature ranged from approximately 16° C. at night to 23° C. during the day and 15C at night. Measurements and numerical values represent averages of typical flowering types. No chemical or photoperiodic treatments were given.

Botanical classification: *Bougainvillea spectabilis* cultivar 'RIJNBO710'.

PROPAGATION

Time to rooting: 8 to 10 days at approximately 25° C.

Root description: Fine, fibrous, well branched.

PLANT

Growth habit: Upright tender perennial, suitable for indoor ornamental use or outdoor garden use in warm climates.

Height: Approximately 73.5 cm.
Plant spread: Approximately 22.8 cm.
Growth rate: Moderate. Approximately 10 cm per month during Spring.
Branching characteristics: Not free branching, moderate without pinching.
Length of lateral branches: Average 39.6 cm.
Diameter of lateral branches: Approximately 0.5 cm.
Quantity of lateral branches: Average 2.
Texture of lateral branches: Dull, smooth.
Color of lateral branches: Younger stem: Near RHS Yellow-Green 146A. Older stems: near RHS Greyed-Green 197A with stripes of 197C to 197D.
Aspect: Upright.
Number of leaves per lateral branch: Average 16.
Age of plant described: Approximately 1 year old.

FOLIAGE

Leaf:
- *Arrangement.*—Alternate, simple.
- *Average length.*—Approximately 10.8 cm.
- *Average width.*—Approximately 6.1 cm.
- *Shape of blade.*—Ovate.
- *Apex.*—Apiculate.
- *Base.*—Attenuate.
- *Attachment.*—Stalked.
- *Margin.*—Entire.
- *Texture of top surface.*—Smooth, glossy.
- *Texture of bottom surface.*—Moderately glossy. Sparcely covered with very short hairs. Avg. length: 0.5 mm. Color: Near RHS Green-White 157D.
- *Leaf internode length.*—Approximately 0.24 cm.
- *Color.*—Young foliage upper side: Near RHS Green 143A. Young foliage under side: Near RHS Yellow-Green 146B. Mature foliage upper side: Near RHS Green to Yellow-Green; between 137A and 147A, but, darker. Mature foliage under side: Near RHS Green 137C to 138A.
- *Venation.*—Type: Pinnate. Venation color upper side: Near RHS Green 143A. Venation color under side: Near RHS Yellow-Green 144B to 144C.

Petiole:
- *Length.*—Average 3.0 cm.
- *Width.*—Average 0.2 cm.
- *Coloration.*—Near RHS Yellow-Green 144B.

Other characteristics: One thorn is above each leaf.
- *Average thorn length.*—0.5 cm.
- *Average thorn width at base.*—0.1 cm.
- *Thorn coloration.*—Near RHS Greyed-Orange 166A.

FLOWER

Bloom period: Continuously from March to October.

Bud:
- *Bud shape.*—Oblanceolate with a rounded top.
- *Bud length.*—Average 1.4 cm.
- *Bud diameter.*—Approximately 0.2 cm.
- *Bud color.*—Near RHS Green 138A, Top Red-Purple 63C.
- *Rate of opening.*—Flowers open approximately 1 week after described bud stage.

Inflorescence:
- *Form.*—Axillary, compound cyme.
- *Width of entire inflorescence.*—Average 10.0 cm.
- *Height of entire inflorescence.*—Average 8.4 cm.
- *Quantity of individual flowers in inflorescence.*—Avg. 63.

Individual flowers:
- *Form.*—Single, tubular flowers growing from the base of a single bract. Staminate flowers consisting of anthers only, no petals, no sepals, each "flower" is supported by one conspicuous gland. Individual (staminate) flowers are grouped in five, supported by two conspicuous bracts.
- *Quantity per lateral stem.*—Avg. 500.
- *Depth.*—Approximately 1.7 cm.
- *Diameter.*—Approximately 0.8 cm.
- *Aspect.*—Upright to outward.
- *Petals.*—Texture: Smooth, slightly crinkled. Petal Arrangement: Rotate, fused tubular. Petal Quantity: Approximately 5. Shape: Narrowly flabellate, 95% of length fused. Margin: Fused, only tips free. Tip: Cleft. Length: Approximately 1.7 cm. Width: Unfused tips, 0.35 mm. Petal Color: Upperside when opening: Near RHS Green-White 157B. Center near Yellow-Green 149A. Upperside mature: Near RHS Green-White 157B. Center near Yellow-Green 149A. Underside when opening: Near RHS Green-White 157B to 157C. Underside mature: Near RHS Green-White 157B to 157C.
- *Duration on plant.*—Approximately 1 week. Self-cleaning.

Fragrance: None.

Sepals:
- *Arrangement/shape.*—Trumpet-shaped, fused 90% along length.
- *Quantity.*—Approximately 5.
- *Margin.*—Entire.
- *Tip.*—Acute.
- *Length.*—Approximately 1.6 cm.
- *Width.*—Approximately 0.1 cm.
- *Color.*—Upperside Immature: Near RHS Green 138A and 138C. Upperside Mature: Near RHS Green 138A to 138C Top Green-White 157B. Underside Immature: Near RHS Green 138A to 138C Top Red-Purple 63C. Upperside Mature: Near RHS Green 138A to 138C Top Red-Purple 63C to 63D.

Calyx:
- *Shape.*—Trumpet-shaped.
- *Base.*—Reniform.
- *Length.*—Approximately 1.7 cm.
- *Diameter.*—Approximately 0.8 cm.

Peduncle:
- *Length.*—Approximately 2.4 cm.
- *Diameter.*—Approximately 0.2 cm.
- *Angle.*—Average angle 50° from stem.
- *Color.*—Near RHS Yellow-Green 146A.

Pedicels:
- *Arrangement.*—Individual flowers in whorls of 3, together on pedicels. Each individual flower sessile, implanted in a colorful bract.
- *Length.*—Approximately 1.7 cm.
- *Diameter.*—Approximately 0.1 cm.
- *Angle.*—Central flowers occur straight up, other flowers in whorl at an average angle of 30°.
- *Strength.*—Moderately strong.
- *Color.*—Near RHS Yellow-Green 144A.

Other floral characteristics: Behind every individual flower there is one bract,

*Bracts.*—Shape: Broadly ovate. Length: Approximately 3.6 cm. Width: Approximately 3.0 cm. Tip: Abruptly acute. Base: Cordate. Margin: Entire Aspect: Undulating. Color: Both sides of immature bract: Near RHS Red-Purple 71C. Upper side of mature bract: Near RHS Red-Purple N74B Under side of mature bract: Near RHS Red-Purple N74B, Bract vein color on both sides: Near RHS Yellow-Green 146A.

REPRODUCTIVE ORGANS

Androecium:

*Stamen quantity.*—Approximately 6.
*Anther length.*—Approximately 0.05 cm.
*Anther color.*—Near RHS Yellow 13A.
*Pollen color.*—Near Yellow 13B to 13C.
*Pollen quantity.*—Low.

Gynoecium:

*Pistil quantity.*—1.
*Pistil length.*—Approximately 0.5 cm.
*Stigma shape.*—Lineate.
*Stigma color.*—Near RHS White N155A.
*Style length.*—Approximately 0.2 cm.
*Style color.*—Near RHS Yellow-Green 144B.
*Ovary color.*—Near RHS Yellow-Green 144B.

OTHER CHARACTERISTICS

Disease resistance: Neither resistance nor susceptibility to diseases or pests has been observed in this variety.

Drought tolerance and temperature tolerance: Tender perennial, low temperature tolerance is unknown. Tolerates high temperature to at least 35° C. No drought tolerance has been observed.

Fruit/seed production: Fruits and seeds have not been observed.

What is claimed is:

1. A new and distinct cultivar of *Bougainvillea* plant named 'RIJNBO710' as herein illustrated and described.

* * * * *